United States Patent [19]

Roy et al.

[11] Patent Number: 4,758,443

[45] Date of Patent: Jul. 19, 1988

[54] THIETANYL-SUBSTITUTED AMIDES AND USE THEREOF AS SWEETENERS

[75] Inventors: Glenn M. Roy, Garnerville; Ronald E. Barnett, Suffern; Paul R. Zanno, Nanuet, all of N.Y.

[73] Assignee: General Foods Corporation, White Plains, N.Y.

[21] Appl. No.: 875,854

[22] Filed: Jun. 18, 1986

[51] Int. Cl.[4] .................... A23L 1/236; C07D 331/04
[52] U.S. Cl. ........................................ 426/548; 549/88
[58] Field of Search ........................... 426/548; 549/88

[56] References Cited

U.S. PATENT DOCUMENTS

| | | | |
|---|---|---|---|
| 4,375,430 | 3/1983 | Skavounos | 549/88 |
| 4,454,328 | 6/1984 | Brennan | 549/88 X |
| 4,465,626 | 8/1984 | Skavounos | 549/88 |
| 4,619,834 | 10/1986 | Zanno et al. | 426/548 |
| 4,622,232 | 11/1986 | Zanno et al. | 426/548 |
| 4,636,396 | 1/1987 | Zanno et al. | 426/548 |
| 4,638,071 | 1/1987 | Barnett et al. | 549/88 |
| 4,650,688 | 3/1987 | Roy et al. | 426/548 |
| 4,652,457 | 3/1987 | Zanno et al. | 426/548 |
| 4,654,219 | 3/1987 | Barnett et al. | 426/548 |
| 4,654,439 | 3/1987 | Roy et al. | 426/548 |
| 4,666,729 | 5/1987 | Roy et al. | 426/548 |
| 4,676,989 | 6/1987 | Barnett et al. | 426/548 |
| 4,678,674 | 7/1987 | Zanno et al. | 426/548 |
| 4,678,675 | 7/1987 | Zanno et al. | 426/548 |
| 4,698,231 | 10/1987 | Barnett et al. | 426/548 |
| 4,701,552 | 10/1987 | Zanno et al. | 426/548 |

OTHER PUBLICATIONS

The Procter & Gamble Co., European Patent Application 0168112, published 1-15-86, 46 pages.

Primary Examiner—Joseph Golian
Attorney, Agent, or Firm—Linn I. Grim; Daniel J. Donovan

[57] ABSTRACT

This invention is directed to food sweeteners of the formula:

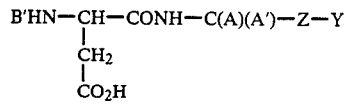

wherein

A is hydrogen, alkyl containing 1-3 carbon atoms, hydroxyalkyl containing 1-3 carbon atoms, alkoxymethyl wherein the alkoxy contains 1-3 carbon atoms or carbalkoxy wherein the alkoxy group contains 1-3 carbon atoms;

A' is hydrogen or alkyl containing 1-3 carbon atoms;

A and A' taken together with the carbon atom to which they are attached form cycloalkyl containing 3-4 carbon atoms;

Z is $-CH_2CH_2-$; $-CH=CH$;

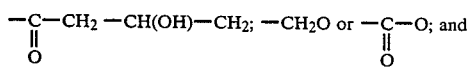

Y is thietanyl or alkyl-substituted thietanyl containing up to a total of 8 carbon atoms;

B' is H or an amino protecting group with the proviso that when Z is

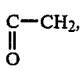

B' is not H;

and food acceptable salts thereof.

49 Claims, No Drawings

THIETANYL-SUBSTITUTED AMIDES AND USE THEREOF AS SWEETENERS

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, often times the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweeteners are disclosed. In the background of this patent a generic formula is described as an attempt to represent dipeptide sweeteners disclosed in five prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969; and German Pat. No. 2,054,554. The general formula attempting to represent these patents is as follows:

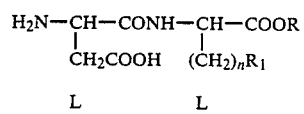

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $S(O)_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartylmethionine methyl esters are disclosed by Brussel, Peer and Van der Heijden in *Chemical Senses and Flavour*, 4, 141–152 (1979) and in *Z. Lebensm. Untersuch-Forsch*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan, et al. sweeteners having the following formulas are disclosed:

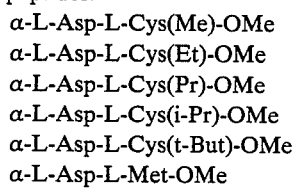

and physiologically acceptable cationic and acid addition salts thereof wherein $R^a$ is $CH_2OH$ or $CH_2OCH_3$;

R is a branched member selected from the group consisting of fenchyl, diisopropylcarbinyl, d-methyl-t-butylcarbinyl, d-ethyl-t-butyl-carbinyl, 2-methylthio-2,4-dimethyl-pentan-3-yl, di-t-butylcarbinyl,

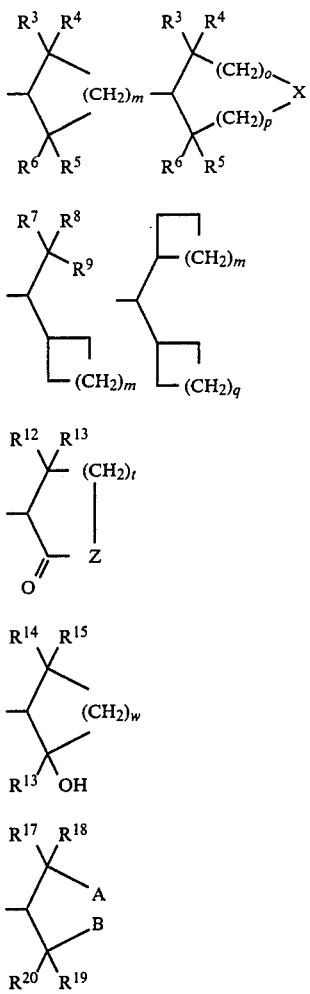

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides or L-aspartyl-D-serinamides.

European Patent Application No. 95772 to Tsau describe aspartyl dipeptide sweeteners of the formula:

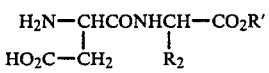

wherein R' is alkyl of 1 to 6 carbons, and $R_2$ is phenyl, phenylalkenyl or cyclohexylalkenyl, wherein the alkenyl group has 1 to 5 carbons. Closely related is U.S. Pat. No. 4,439,460 to Tsau, et al. which describes dipeptide sweeteners of the formula:

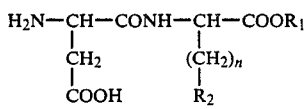

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al. $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkadienyl, or $S(O)_m$ lower alkyl provided that n is 1 or 2 and m is 0 or 2. Closely related are U.S. Pat. Nos. 4,448,716; 4,153,737; 4,031,258; 3,962,468; 3,714,139; 3,642,491; and 3,795,746.

U.S. Pat. No. 3,803,223 to Mazur, et al. describe dipeptide sweeteners and anti-inflammatory agents having the formula:

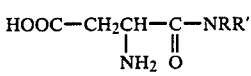

wherein R is hydrogen or a methyl radical and R' is a radical selected from the group consisting of alkyl, or

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

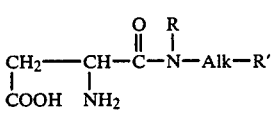

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

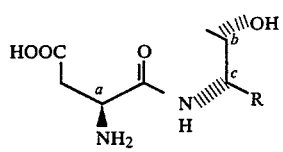

wherein R is $C_4$–$C_9$ straight, branched or cyclic alkyl, and wherein carbons a, b and c have the (S) configuration.

European Patent Application No. 48,051 describes dipeptide sweeteners of the formula:

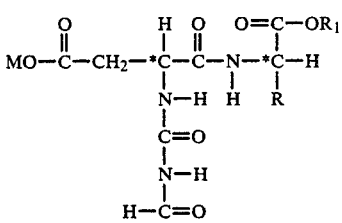

wherein

M represents hydrogen, ammonium, alkali or alkaline earth,

R represents

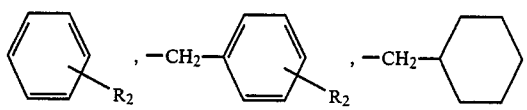

R₁ represents methyl, ethyl, propyl;

R₂ represents —OH, or CH₃;

* Signifies an L-optical configuration for this atom.

Dutch Patent Application No. 7207426 discloses L-aspartyl-3-fenchylalanine methyl ester as a sweetening agent.

U.S. Pat. No. 3,971,822 to Chibata, et al., disclose sweeteners having the formula:

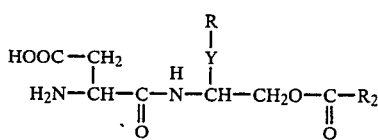

wherein R' is hydrogen or hydroxy, R₂ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its physiologically acceptable salts as useful sweeteners. U.S. Pat. No. 3,959,245 disclose the 2-methyl cyclohexyl analog of the abovementioned patent.

U.S. Pat. No. 3,920,626 discloses N-α-L-aspartyl derivatives of lower alkyl esters of O-lower-alkanoyl-L-serine, β-alanine, α-aminobutyric acid an D-β-aminobutyric acid as sweeteners.

Miyoshi, et al. in *Bulletin of Chemical Society of Japan*, 51, p. 1433-1440 (1978) disclose compounds of the following formula as sweeteners:

wherein R' is H, CH₃, CO₂CH₄, or benzyl and R₂ is lower alkyl or unsubstituted or substituted cycloalkyl.

European Patent Application No. 128,654 describes gem-diaminoalkane sweeteners of the formula:

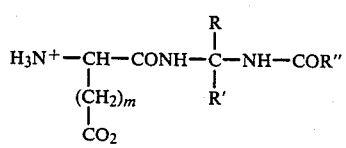

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

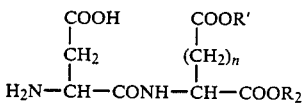

wherein R' is a branched or cyclic alkyl group of 3 to 8 carbon atoms, R₂ is a lower alkyl group of 1 to 2 carbon atoms and n is a integer of 0 or 1.

European Patent Application No. 34,876 describes amides of L-aspartyl-D-amino acid dipeptides of the formula:

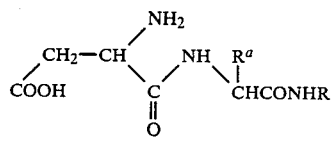

wherein $R^a$ is methyl, ethyl, n-propyl or isopropyl and R is a branched aliphatic, alicyclic or heterocyclic member which is branched at the alpha carbon atoms and also branched again at one or both of the beta carbon atoms. These compounds are indicated to be of significant sweetness.

In the *Journal of Medicinal Chemistry*, 1984, Vol. 27, No. 12, pp. 1663-8, are described various sweetener dipeptide esters, including L-aspartyl-α-aminocycloalkane methyl esters.

The various dipeptide esters of the prior art have been characterized as lacking significant stability at low pH values and/or thermal stability. These characterstics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are amides of aspartic acid and certain amines which are characterized by the presence of a thietanyl substituent and are low caloric sweeteners possessing a high order of sweetness with pleasing taste and a high order of stability to acid pH and elevated temperatures compared to known dipeptide sweeteners.

This invention provides new sweetening compounds represented by the formula:

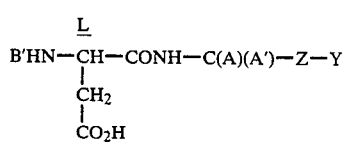

wherein

A is hydrogen, alkyl containing 1-3 carbon atoms, hydroxyalkyl containing 1-3 carbon atoms, alkoxymethyl wherein the alkoxy contains 1-3 carbon atoms or carbalkoxy wherein the alkoxy group contains 1-3 carbon atoms;

A' is hydrogen or alkyl containing 1-3 carbon atoms;

A and A' taken together with the carbon atom to which they are attached form cycloalkyl containing 3-4 carbon atoms;

Z is —CH₂CH₂—; —CH═CH;

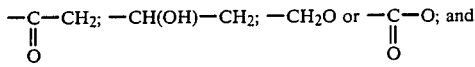

Y is thietanyl or alkyl-substituted thietanyl containing up to a total of 8 carbon atoms;

B' is H or an amino protecting group with the proviso that when Z is

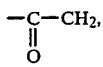

B' is not H.

and food acceptable salts thereof.

DESCRIPTION OF THE PREFERRED EMBODIMENTS

In accordance with the present invention, the preferred compounds are those wherein the thietanyl moiety is substituted with at least one lower alkyl group; preferably a beta-position on the thietanyl ring, i.e., the β or β' carbon atoms. Among these the preferred are thietanyl moieties disubstituted in the beta position with alkyl groups. Particularly preferred are thietanyl groups which are alkyl substituted in the β,β and β',β' positions, i.e., tetramethyl thietanyl. Of the alkyl groups, the most preferred is methyl. Thus, preferred thietanyl groups include 2,4-dimethyl-; 2,2-dimethyl-; 2,2,4-trimethyl-; 2,4,4-trimethyl-; 4,4-dimethyl-; β-isopropyl-; β,β'-diethyl-; β-tertiarybutyl-; and 2,2,4,4-tetramethylthietanyl groups. In all cases, the thietanyl moieties may contain up to a total of 8 carbon atoms including the four ring carbon atoms. The preferred thietanyl groups are attached to the remainder of the present new compounds at the 3-position.

Also preferred are compounds in which Z is —CH₂—CH₂—, —CH═CH—; —CH(OH)—CH₂— and

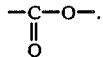

Of these, compounds in which Z is —CH═CH— are also useful intermediates for preparing those in which Z is —CH₂—CH₂—. Compounds in which Z is

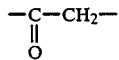

are also useful intermediates for preparation of compounds in which Z is —CH(OH)—CH₂—. When Z is

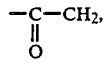

it is preferred that B' is an amino protecting group in order to avoid any possible internal cyclization with the amino group. In both cases, such preparations are effected by known reduction techniques;

When Z is other than

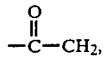

it is preferred that B' is H.

The amino protecting group representative of the substituent B' in Formula I is an electron-withdrawing protecting group. Exemplary protecting groups include COCF₃, COOCl₃, and CONAr—X, wherein Ar is aryl, X is NO₂, CN, COOR", COR", SO₂R", halo, carboxy, SO₃H, SO₃R", SO₂NR"R", SO₂NH R", SO₂NH₂, CONR"R", CONHR", CONH₂, SOR",

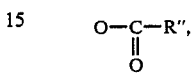

OR", OSO₂R", OCF₃, CH₂OR", CH(OR")₂, COCF₃, CF₃, CH₂CF₃, CCl₃, C$_t$F$_{2t+1}$, and the like;

wherein each R" is the same or different and is C₁–C₁₂ alkyl and t is an integer from 1–6.

Preferable X groups are CN, COOC₂H₅, COOCH₃, SO₂CH₃ or COCH₃ groups.

The term aryl when used hereinabove signifies a 6-10 membered aromatic ring compounds and includes phenyl, α-naphthyl, β-naphthyl and the like.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, metahydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. The general reaction scheme involves amide formation between an acylating derivative of aspartic acid and amines of Formula II:

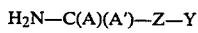

wherein A, A', Z and Y have the same meaning as previously described. Acylating derivatives of aspartic acid are well-known and include, for example, aspartic anhydride, including mixed anhydrides with lower alkanoic acids and half-esters of aspartic acid. In the amide-forming reactions, it is preferred to employ protecting groups which preclude undesired side reactions as exemplified in the following sequence:

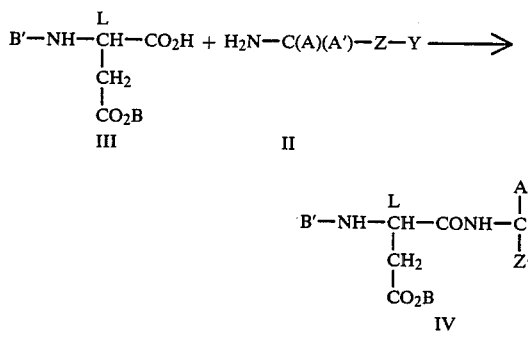

In these, group B' is an amino protecting group, B is a carboxyl protecting group and the remaining groups have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for B' and benzyl for B. When A includes a free hydroxy group suitable protecting groups can be employed as known in the art.

Coupling of compounds with general formula II to compounds having general formula III employs established amide-forming techniques. One such technique uses dicyclohexylcarbodiimide (DCC) as the coupling agent. The DCC method may be employed with or without additives such as 4-dimethylaminopyridine or copper(II). The DCC coupling reaction generally proceeds at room temperature, however, it may be carried out from about −20° to 50° C. in variety of solvents inert to the reactants. Thus suitable solvents include, but are not limited to, N,N-dimethylformamide, methylene chloride, toluene and the like. Preferably the reaction is carried out under an inert atmosphere such as argon or nitrogen. Coupling usually is complete within 2 hours but may take as long as 24 hours depending on reactants.

Various other amide-forming methods can be employed to prepare the desired compounds using suitable derivatives of the free-carboxy group in compounds of structure II, e.g., acid halide, mixed anhydride with acetic acid and similar derivatives. The following illustrates such methods using aspartic acid as the amino dicarboxylic acid.

One such method utilizes the reaction of N-protected aspartic anhydrides with the selected amino compound of formula III. Thus compounds of formula III can be reacted directly in inert organic solvents with L-aspartic anhydride having its amino group protected by a formyl, carbobenzloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula III in an organic solvent capable of dissolving both and inert to the same. Representative solvents are ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Compounds of Formula II, that is the amino compounds, can be prepared by art-recognized procedures.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium; potassium, lithium, or the alkaline earth metal salts such as calcium or magnesium, as well as aluminum, zinc and like salts.

Conversion of the present new compounds of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterisk(*) in the formula below, and at least one pseudo-asymmetric site which is designated by a double asterisk(**):

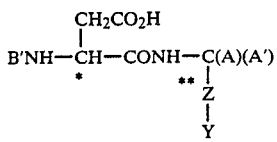

There may also be asymmetric sites in Z and Y depending on the nature of the substituents. Whenever A is identical to A', the compounds of the present invention have one asymmetric site, designated by the asterisk, in the dicarboxylic acid moiety, and may have others depending upon the nature of Z and Y. Although both the D and L forms are possible, the preferred compounds are those in which the dicarboxylic acid group is in the L-configuration. Whenever the groups A' and A are different, the carbon atoms designated by the double asteriks become asymmetric centers and the compounds of the present invention will contain at least two asymmetric centers. Regardless, the configuration around each of the asymmetric sites, whenever present, may exist in either the D and L forms, and all possible stereoisomers are contemplated to be within the scope of the present invention. Since the aspartyl group is in the L-configuration, whenever an asymmetric center is present at any of the other possible asymmetric sites, the compounds of the present invention are diastereomers, which can be separated, if desired, by art-recognized techniques, as, for examples, chromatography. However, mixtures of at least two stereoisomers will also exhibit sweetness properties and are useful as sweeteners.

The following examples further illustrate the invention.

EXAMPLE 1

N-alpha-L-aspartyl-2-amino-4-(2,2,4,4-tetramethylthietan-3-yl)trans-3-butene

A. Homologation of diethylmalonate

To a stirring mixture of NaH (12.49 g, 0.52 mol) in 300 mls of anhydrous THF at 0° C. under argon, was added 50 g (0.312 mol) of diethyl malonate. The reaction stirred for 0.5 hours as hydrogen gas evolved. Once the complete formation of the anion was certain, 25.17 mls (23.09 g, 0.312 mol) of ethyl formate was added dropwise over a period of ten minutes. The solution was allowed to stir for two hours and was then quenched by the addition of 200 mls of saturated ammonium chloride. The reaction was extracted three times with 100 ml portions of diethyl ether. The organic portions were combined and washed once with saturated sodium bicarbonate, once with water, and dried over anhydrous magnesium sulfate. The ethereal solution was filtered, concentrated, and purified by flash chromatography to yield the desired product as a colorless oil.

B. 2,4-Dihydro-2,4-dimethyl-3-formylpentane

The homologated diester (25 g, 0.136 mol) was placed in a two-necked flask along with 135 mls of diethyl ether at −78° C. under argon. 5 Equivalents of methylmagnesium bromide (226 mls, 0.68 mol) was then added slowly to the well-mixed solution. The reaction stirred for two hours when 200 mls of saturated ammonium chloride was introduced to the reaction. After fifteen minutes of agitation, the mixture was extracted three times with 100 ml portions of diethyl ether. The ethereal extracts were combined and washed once with 100 mls of saturated sodium bicarbonate, and once with 100 mls of water. The organic layers were combined, dried over magnesium sulfate, filtered, and concentrated. Chromotographic purification resulted in the isolation of the desired di-carbinol.

C. 2,4-Dibromo-2,4-dimethyl-3-formylpentane

To a magnetically stirred solution of N-bromosuccinimide (28.48 g, 0.16 mol) in THF (500 mls), a solution of triphenylphosphine (41.92 g, 0.16 mol) in THF was added dropwise; and exothermic reaction resulted with a white solid separating. To this suspension, a solution of dicarbinol (12 g, 0.08 mol) in THF, was added and stirring was continued until the solid went into solution. The mixture was concentrated in vacuo and the residue was treated with water and ether. The organic layer was separated, washed with water, dried over magnesium sulfate, and concentrated to afford the desired product.

D. 1-(2,4-Dibromo-2,4-dimethyl-3-pentyl)buten-1-ol

To a magnetically stirred solution of 6.05 g (0.05 mol) of 1-bromopropene in 200 mls of Trapp mixture (THF/diethylether/pentane 4:1:1) was cooled under argon to −120° C. After ten minutes of stirring, tert-butyl lithium (59 mls, 0.001 mol) was added to the mixture. The product from the previous reaction (12.87 g, 0.045 mol) was added and stirring continued for fifteen minutes at −78° C. and for twenty minutes at room temperature. The mixture was quenched by pouring into a separatory funnel containing 0.01 mol of acetic acid, saturated sodium chloride and methylene chloride. The organic layer was separated, dried over magnesium sulfate, and concentrated to afford the desired allylic alcohol.

E. 1-(2,4-Dibromo-2,4-dimethyl-3-pentyl)-2-butenyl-1-(2,2,2-trichloroacetimidate)

A flame dried three necked flask containing a solution of 15 g (0.046 mol) of 1-(2,4-dibromo-2,4-dimethyl-3-pentyl)-2-buten-1-ol in 45 mls of anhydrous THF (1M) at 0° C. under argon was treated portionwise with a hexane slurry of 0.37 g (0.0092 mol) of potassium hydride (a 35% dispersion in mineral oil which had been washed twice with hexane). After stirring for ten minutes, hydrogen evolution ceased. The yellow alkoxide solution was transferred, via a double needle syringe, to a solution of 4.6 mls (0.046 mol) of trichloroacetonitrile in 100 mls of diethyl ether at 0° C. under argon. The resulting mixture darkened quickly and was allowed to stir at 0° C. for 2 hours. The mixture was taken up in 200 mls of 1% ethanolic hexane and shaken vigorously for two minutes. Dark insoluble material precipitated and was promptly filtered. The filtrate was then concentrated to afford the crude acetimide.

F. 2,2,2-Trichloro-N-[2-methyl-3-butenyl-4-(2,4-dibromo-2,4-dimethyl-3-pentane)-1

A solution of crude imidate (21.6 g, 0.046 mol) in 200 mls of xylene was brought to reflux and monitored by IR. After 3 hours, the isomerization was complete. Concentration in vacuo afforded the crude acetamide.

G. Preparation of 2-amino-4-(2,2,4,4-tetramethyl thietanyl)-3-butene

Sodium metal (2.12 g, 0.092 mol) was dissolved in 50 mls of anhydrous methanol and the mixture was then cooled to 0° C. Hydrogen sulfide gas was passed through the mixture until a saturated solution was obtained. Then the crude acetamide (0.046 mol) was added dropwise in methanol while continuing to allow hydrogen sulfide to pass through the reaction mixture. After the addition was complete, the reaction was stirred for two hours at 0° C., allowed to warm to room temperature and stirred overnight. After pouring the mixture into water, it was extracted with diethyl ether and the extracts washed with 1M HCL and saturated sodium chloride. After drying over magnesium sulfate, filtering and concentration resulted in the product which was used without purification.

H. Preparation of Dipeptide

To a three necked flask equipped with an overhead stirrer, was added 0.98 g (0.0046 mol) of 2-amino-3-butenyl-4-(1,1,3,3-tetramethylthietane) in 10 mls of water. The solubility of the amine was enhanced by the addition of 4 mls of THF. The flask was cooled to 0° C. and 0.80 g (0.0046 mol) of NTA was added in small portions. A pH of 11 was recorded prior to the NTA addition and decreased to a range of 8.5–9.5 during the addition. Once the addition was complete, the pH stabilized at 10.5. After 2 hours of stirring, the mixture was acidified with concentrated HCl to a pH of 4.5. The mixture was filtered through Celite, washed through with 25 mls of methanol, and concentrated in vacuo. The crude product was purified by reversed phase flash chromatography using 70% methanol-water as an eluant to afford the desired product as a white solid.

Using the foregoing procedure, the following products are obtained from corresponding starting compounds:

N-α-L-aspartyl-2-amino-2-methyl-4-(2,2,4,4-tetramethylthietan-3-yl)-trans-3-butene;
N-α-L-aspartyl-2-amino-2-methyl-4-(2,4-dimethylthietan-3-yl)-trans-3-butene;
N-α-L-aspartyl-2-amino-2-methyl-4-(2,2-dimethylthietan-3-yl)-trans-3-butene;
N-α-L-aspartyl-2-amino-2-methyl-4-(2,2,4-trimethylthietan-3-yl)-trans-3-butene;
N-α-L-aspartyl-2-amino-2-methyl-4-(2,4,4-trimethylthietan-3-yl)-trans-3-butene;
N-α-L-aspartyl-2-amino-2-methyl-4-(4,4-dimethylthietan-3-yl)-trans-3-butene;
N-α-L-aspartyl-2-amino-2-methyl-4-(β,β'-diethylthietan-3-yl)-trans-3-butene;
N-α-L-aspartyl-2-amino-2-methyl-4-(β-tertbutylthietan-3-yl)-trans-3-butene;
N-α-L-aspartyl-2-amino-4-(2,4-dimethylthietan-3-yl)-trans-3-butene;
N-α-L-aspartyl-2-amino-4-(2,2-dimethylthietan-3-yl)-trans-3-butene;
N-α-L-aspartyl-2-amino-4-(2,2,4-trimethylthietan-3-yl)-trans-3-butene;
N-α-L-aspartyl-2-amino-4-(2,4,4-trimethylthietan-3-yl)-trans-3-butene;
N-α-L-aspartyl-2-amino-4-(4,4-dimethylthietan-3-yl)-trans-3-butene;
N-α-L-aspartyl-2-amino-4-(β,β'-diethylthietan-3-yl)-trans-3-butene;
N-α-L-aspartyl-2-amino-4-(β-tertbutylthietan-3-yl)-trans-3-butene;
N-α-L-aspartyl-2-amino-1-methoxy-4-(2,2,4,4-tetramethylthietan-3-yl)-trans-3-butene;
N-α-L-aspartyl-2-amino-1-hydroxy-4-(2,2,4,4-tetramethylthietan-3-yl)-trans-3-butene;
N-α-L-aspartyl-2-amino-4-(2,2,4,4-tetramethylthietan-3-yl)-trans-3-butenoic acid methyl ester;
N-α-L-aspartyl-1-amino-1-[2-(2,2,4,4-tetramethylthietan-3-yl)-trans-ethenyl]cyclopropane.

EXAMPLE 2

N-Alpha-L-aspartyl-2-amino-4-(2,2,4,4-tetramethylthietan-3-yl)butane

Method A

The product from Part F of Example 1 is treated with H₂ gas at 45 psi over 5% Pd/C until reduction of the double bond is completed and the product is obtained from the reaction mixture by filtration and evaporation.

Method B

The crude acetamide from paragraph F, Example 1, was dissolved in 100 mls of ethanol and placed in an ultrasound bath. This vessel was then purged with argon. Cyclohexadiene (10 equiv.) was added, followed by 0.1 equivalents of 10% Pd/C. Ultrasound was commenced for one-half hour. After one half hour the reaction was completed, as indicated by TLC. The solution was filtered through Celite and concentrated to afford the desired product which was used to prepare the saturated analogue of the product from step H.

The reaction product is then converted to the dipeptide by the procedure of paragraphs 7 and 8 of Example 1.

Using these procedures, the following products are produced from the corresponding unsaturated compound.

N-α-L-aspartyl-2-amino-2-methyl-4-(2,2,4,4-tetramethylthietan-3-yl)butane;
N-α-L-aspartyl-2-amino-2-methyl-4-(2,4-dimethylthietan-3-yl)butane;
N-α-L-aspartyl-2-amino-2-methyl-4-(2,2-dimethylthietan-3-yl)butane;
N-α-L-aspartyl-2-amino-2-methyl-4-(2,2,4-trimethylthietan-3-yl)butane;
N-α-L-aspartyl-2-amino-2-methyl-4-(2,4,4-trimethylthietan-3-yl)butane;
N-α-L-aspartyl-2-amino-2-methyl-4-(4,4-dimethylthietan-3-yl)butane;
N-α-L-aspartyl-2-amino-2-methyl-4-(β,β'-diethylthietan-3-yl)butane;
N-α-L-aspartyl-2-amino-2-methyl-4-(β-tertbutylthietan-3-yl)butane;
N-α-L-aspartyl-2-amino-4-(2,4-dimethylthietan-3-yl)butane;
N-α-L-aspartyl-2-amino-4-(2,2-dimethylthietan-3-yl)butane;
N-α-L-aspartyl-2-amino-4-(2,2,4-trimethylthietan-3-yl)butane;

N-α-L-aspartyl-2-amino-4-(2,4,4-trimethylthietan-3-yl)butane;

N-α-L-aspartyl-2-amino-4-(4,4-dimethylthietan-3-yl)butane;

N-α-L-aspartyl-2-amino-4-(β,β'-diethylthietan-3-yl)butane;

N-α-L-aspartyl-2-amino-4-(β-tertbutylthietan-3-yl)butane;

N-α-L-aspartyl-2-amino-1-methoxy-4-(2,2,4,4-tetramethylthietan-3-yl)butane;

N-α-L-aspartyl-2-amino-1-hydroxy-4-(2,2,4,4-tetramethylthietan-3-yl)butane;

N-α-L-aspartyl-2-amino-4-(2,2,4,4-tetramethylthietan-3-yl)butanoic acid methyl ester;

N-α-L-aspartyl-1-amino-1-[2-(2,2,4,4-tetramethylthietan-3-yl)-ethyl]cyclopropane.

EXAMPLE 3

(2,2,4,4-Tetramethyl thietanyl) N-alpha-L-aspartyl-2-amino isobutyrate

A. N-Boc-2-amino isobutyric acid 2-amino isobutyric acid was N-Boc protected as described in the literature in 62% yield. (J. Miss. Acad. Sci. 29, 13, 1984).

B. (2,2,4,4-tetramethyl thietanyl) N-Boc-2-amino isobutyrate

The N-protected amino acid (3.7 g, 18.3 mmol) was dissolved in 1,2-dichloroethane (50 ml) at 0° C. under argon. A solution of N,N-dimethylamino pyridine (0.5 equiv.) and 2,2,4,4-tetramethyl thietanyl alcohol (1 equiv.) in 1,2-dichloroethane (10 ml) was added. Lastly, dicyclohexylcarbodiimide (1.1 equiv.) was added as a solid. After five days of stirring at room temperature, the urea was removed by filtration and the filtrate was hi-vacuum rotary evaporated and then diluted with petroleum ether (50 ml). The solution was clarified again by filtration and the filtrate was hi-vacuum rotary evaporated to a paste. Column chromatography on silica gel with 6:1 petroleum ether/ethyl acetate gave the pure product (4.4 g) in 81% yield as a white crystalline solid. The structure of the product was confirmed by 300 MHz proton and carbon NMR and FAB mass spectrometry. NMR (CDCl$_3$) δ 1.44 (s, 9H), 1.54 (s, 6H), 1.55 (d, 12H), 5.0 (s, 1H).

C. (2,2,4,4-tetramethyl thietanyl)2-Aminoisobutyrate

A fresh solution of trimethylsilyl iodide was prepared at 0° C. under argon by dissolving 1.47 g of sodium iodide in 20 ml of acetonitrile. Then 1.26 ml of trimethylsilyl chloride was added and and the mixture was stirred until a yellowish color developed over 0.5 hours. The N-Boc protected amino ester from above, 1.14 g, was dissolved in 75 ml of chloroform at 0° C. and 13.84 ml of the trimethylsilyl iodide solution was added via syringe. The reaction was stirred for 2 hours to room temperature and then quenched with 20 ml methanol and hi-vacuum rotary evaporated to a solid. The solid was washed with diethyl ether and characterized to be the ammonium iodide salt of the desired product. Yield: 1.4 g.

D. (2,2,4,4-tetramethyl thietanyl) N-Alpha-L-aspartyl-2-aminoisobutyrate

The salt from above, 360 mg, was dissolved in 6 ml of water of 0° C. and adjusted to pH 9.1 with 1N NaOH. 276 mg of N-thiocarboxy-L-aspartic acid anhydride (NTA) was added as a solid slowly while the pH was maintained at 9.0-9.2 with the addition of 1N NaOH. Upon completion of addition of the NTA the pH was adjusted as above for 3 hours. When stabilized, 3 ml of methanol was added and the solution was acidified with 2% hydrochloric acid to pH 4.5. After stirring for 0.5 hours, the mixture was hi-vacuum rotary evaporated to give 680 mg of a solid. The solid was dissolved in methanol and filtered. The filtrate was concentrated to a paste and redissolved in water and applied to an AG-1×4 acetate form ion exchange column. The product eluted with pure water and was hi-vacuum rotary evaporated to give 125 mg of a white solid. The product was characterized by FAB mass spectrometry.

Using these procedures, the following products are produced from the corresponding starting compounds.

(2,4-dimethylthietanyl) N-α-L-aspartyl-2-aminoisobutyrate;

(2,2-dimethylthietanyl) N-α-L-aspartyl-2-aminoisobutyrate;

(2,2-dimethylthietanyl) N-α-L-aspartyl-2-aminoisobutyrate;

(2,2,4-trimethylthietanyl) N-α-L-aspartyl-2-aminoisobutyrate;

(2,4,4-trimethylthietanyl) N-α-L-aspartyl-2-aminoisobutyrate;

(4,4-dimethylthietanyl) N-α-L-aspartyl-2-aminoisobutyrate;

(β,β'-diethylthietanyl) N-α-L-aspartyl-2-aminoisobutyrate;

(β-tert-butylthietanyl) N-α-L-aspartyl-2-aminoisobutyrate;

(2,2,4,4-tetramethylthietanyl) N-α-L-aspartyl-2-amino-1-hydroxymethylpropionate;

(2,2,4,4-tetramethylthietanyl) N-α-L-aspartyl-2-amino-1-methoxymethylpropionate;

(2,2,4,4-tetramethylthietanyl) N-α-L-aspartyl-1-aminocyclopropylcarboxylate.

EXAMPLE 4

A. 3,3-Diisopropyl methyl acrylate

To a dry flask under argon was added diethyl phosphono methyl acetate (1.1 equiv.) in dry benzene. Sodium hydride (60% dispersion in oil) (1.1 equiv.) was added. The solution was warmed to 60° C. until evolution of hydrogen was complete (1.5 h) and a clear mixture was obtained. Diisopropyl ketone (1 equiv.) was dissolved in dry benzene and added to the 60° C. solution from above so as to maintain a gentle reflux. After 1 hour the solution as evaporated to a paste and the residue distilled at reduced pressure to afford the desired product.

B. Gamma, gamma-dibromo diisopropyl methyl acrylate

The product from above was treated with N-bromo succinimide (2.1 equiv.) in dry carbon tetrachloride at 60° C. and when thin layer chromatography indicated no remaining starting material the solution was filtered and rotary evaporated. The oil was carried onto the next step without purification.

C. Gamma, gamma-dibromo diisopropyl methyl acrylate

The unsaturated ester from above was dissolved in a 1:1 mixture of water and dimethylformamide. The solution was treated with chromium sulfate. (A. Zurauiyah and C. E. Castro, Org. Syn. 49, 98, 1969). Aqueous ammonium sulfate workup and ether extraction followed by distillation gave the desired product.

D. Gamma, gamma-dibromo diisopropyl acetic acid

The ester from above in chloroform at 0° C. was treated with the required amount of reagent prepared as described below. A fresh solution of trimethylsilyl iodide was prepared at 0° C. under argon by dissolving 1.47 g of sodium iodide in 20 ml of acetonitrile. Then 1.26 ml of trimethylsilyl chloride was added and the mixture was stirred until a yellowish color developed over 0.5 hours. Workup was done with methanol and high vacuum rotary evaporation to give the crude product which was purified by filtration through neutral alumina with ether.

E. 2,2,4,4-Tetramethyl thietanyl acetic acid

Sodium metal (1 mol) was dissolved in dry methanol (500 ml) at 10° C., and hydrogen sulfide gas was passed through the mixture until it was saturated. The dibromo acid from above (0.33 mol) was added dropwise in methanol while containing to allow hydrogen sulfide to pass into the solution. After 2 hours at the cold temperature the reaction was stirred at room temperature overnight. After pouring into water and ether extraction the aqueous layer was acidified with dilute acetic acid and re-extracted with ether. After drying with magnesium sulfate and rotary evaporation, cooling produced a solid. This material was washed with a minimum of petroleum ether to give a low melting solid.

F. Anhydride Formation 2,2,4,4-tetramethyl thietanyl acetic acid (1 equiv.) was dissolved in dichloromethane at room temperature. Dicyclohexylcarbodiimide (0.5 equiv.) was added and the contents of the flask stirred for 3 days. The urea was removed by filtration and the filtrate was evaporated. The residue was taken up in petroleum ether and refiltered. The clarified filtrate was evaporated and distilled at 0.5 mm Hg. The product anhydride was characterized by IR spectroscopy.

G. Acylation—Decarboxylation

D-alanine (20 g) was dissolved in dimethyl formamide (400 ml) and treated with chlorotrimethylsilane (26.8 g) and stirred at room temperature (1H) until a homogeneous solution was obtained. Meanwhile, N-alpha-t-butyloxycarbonyl beta-t-butyl L-aspartic acid (58 g) was dissolved in a 1:1 mixture of dimethylformamide and tetrahydrofuran (880 ml), cooled to −15° C., and treated with N-methyl morpholine (22.4 ml) and isobutyl chloroformate (26.2 ml). After 10 minutes of activation the precooled solution of D-alanine silyl ester from above was added via double syringe. N-methyl morpholine (22.4 ml) was added again. The reaction was warmed to room temperature slowly and stirred for four hours then acidified to pH 2 with aqueous hydrochloric acid. The product was extracted with chloroform and washed with dilute acid and water several times. After drying with magnesium sulfate and rotary evaporation a white solid was obtained when crystallized with diethyl ether.

N-Boc-L-aspartic acid beta-t-butyl ester alpha-DL-alanine (1 equiv.) was stirred at room temperature under argon with triethylamine (3 equiv.) and N,N-dimethylamino pyridine (0.08 equiv.). The anhydride from F, above (1.5 equiv.) was added and the mixture stirred neat for 3 days. Aqueous dilute acetic acid was added and the mixture extracted with ethyl acetate. The organic layer was washed with ethyl acetate. The organic layer was washed with water and dilute sodium hydrogen carbonate. Drying with magnesium sulfate followed by rotary evaporation gave a semi-solid. Chromatography on silica gel with 2:1 petroleum ether/ethyl acetate afforded the product, N-Boc-L-aspartic acid beta-t-butyl ester alpha-DL-2-amino 4-(2,2,4,4-tetramethyl)thietanyl-3-butanone.

Similarly, using the appropriate starting materials, the following compounds were prepared:

N-Boc-L-aspartic acid-β-t-butyl ester-α-DL-2-amino-4-(2,4-dimethylthietanyl)-3-butanone;

N-Boc-L-aspartic acid-β-t-butyl ester-α-DL-2-amino-4-(2,2-dimethylthietanyl)-3-butanone;

N-Boc-L-aspartic acid-β-t-butyl ester-α-DL-2-amino-4-(2,2,4-trimethylthietanyl)-3-butanone;

N-Boc-L-aspartic acid-β-t-butyl ester-α-DL-2-amino-4-(2,4,4-trimethylthietanyl)-3-butanone;

N-Boc-L-aspartic acid-β-t-butyl ester-α-DL-2-amino-4-(4,4-dimethylthientanyl)-3-butanone;

N-Boc-L-aspartic acid- β-butyl ester-α-DL-2-amino-4-(β,β'-diethylthietanyl)-3-butanone;

N-Boc-L-aspartic acid-β-t-butyl ester-α-DL-2-amino-4-(β-t-butylthientanyl)-3-butanone;

N-Boc-L-aspartic acid-β-t-butyl ester-α-DL-2-amino-2-methyl-4-(2,2,4,4-tetramethyl)thietanyl-3-butanone;

N-Boc-L-aspartic acid-β-t-butyl ester-α-DL-2-amino-1-methoxy-4-(2,2,4,4-tetramethyl)thietanyl-3-butanone;

N-Boc-L-aspartic acid-β-t-butyl ester-α-(DL)-2-amino-1-hydroxy-4-(2,2,4,4-tetramethylthietanyl)-3-butanone;

N-Boc-L-aspartic acid-β-t-butyl ester-α-(DL)-2-amino-4-(2,2,4,4-tetramethylthietanyl)-3-oxybutanoic acid methyl ester;

N-Boc-L-aspartic acid-β-t-butyl ester-α-(DL)-1-amino-1-[(1-oxo-2-(2,2,4,4-tetramethylthietanyl)ethyl]cyclopropane.

EXAMPLE 5

N-alpha-L-aspartyl-DL-2-amino 4-(2,2,4,4-tetramethyl thietanyl) 3-butanol

The amido ketone from Paragraph G, Ex. 4, was dissolved in 95% ethanol at 0° C. Cerium trichloride (hydrate, 2 equiv.) was added and followed by the addition of sodium borohydride (2 equiv.). The milky solution was stirred for one hour to room temperature and then poured into sufficient water and ethyl acetate to break the emulsion. The organic layer was dried and rotary evaporated to give a white solid which was recrystallized with ether/petroleum ether. The pure product was characterized by FAB mass spectrometry.

The protected dipeptide was treated with 2.1 equiv. of trimethylsilyl iodide as described in Part D. The crude reaction mixture was evaporated to a paste and chromatographed on $C_{18}$ reversed phase silica with methanol and water. It was found that severe insolubility in methanol of the $C_2$ L-diastereomers continually precipitated them out of solution. Thus, isolation of the pure sweet dipeptide was an enrichment of the $C_2$ D-diastereomers.

Using these procedures, the following products are produced from the corresponding precursors.

N-α-L-aspartyl-DL-2-amino-4-(2,4-dimethylthietanyl)-3-butanol;

N-α-L-aspartyl-DL-2-amino-4-(2,2-dimethylthietanyl)-3-butanol;

N-α-L-aspartyl-DL-2-amino-4-(2,2,4-trimethylthietanyl)-3-butanol;

N-α-L-aspartyl-DL-2-amino-4-(2,4,4-trimethylthietanyl)-3-butanol;

N-α-L-aspartyl-DL-2-amino-4-(4,4-dimethylthietanyl)-3-butanol;

N-α-L-aspartyl-DL-2-amino-4-(β,β'-diethylthietanyl)-3-butanol;

N-α-L-aspartyl-DL-2-amino-4-(β-t-butylthietanyl)-3-butanol;

N-α-L-aspartyl-DL-2-amino-2-methyl-4-(2,2,4,4-tetramethylthietanyl)-3-butanol;

N-α-L-aspartyl-DL-2-amino-1-hydroxy-4-(2,2,4,4-tetramethylthietanyl)-3-butanol.

N-α-L-aspartyl-DL-2-amino-1-methoxy-4-(2,2,4,4-tetramethylthietanyl)-3-butanol;

N-α-L-aspartyl-DL-2-amino-4-(2,2,4,4-tetramethylthietanyl)-3-hydroxybutanoic acid methyl ester;

N-α-L-aspartyl-1-amino-1-[1-hydroxy-2-(2,4,4,4-tetramethylthientanyl)ethyl]cyclopropane.

All thin layer (TLC) separations were done with Analtech silica (GF) plates and Analtech reverse phase bonded plates. The preparative chromatography was performed on slurry packed flash columns employing J. T. Baker 40 um flash silica. Reversed phase $C_{18}$ silica from J. T. Baker was used for de-blocked dipeptide purification.

What is claimed is:

1. A compound of the formula:

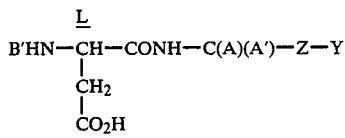

wherein
A is hydrogen, alkyl containing 1–3 carbon atoms, hydroxyalkyl containing 1–3 carbon atoms, alkoxymethyl wherein the alkoxy contains 1–3 carbon atoms or carbalkoxy wherein the alkoxy group contains 1–3 carbon atoms;

A' is hydrogen or alkyl containing 1–3 carbon atoms;

A and A' taken together with the carbon atom to which they are attached form cycloalkyl containing 3–4 carbon atoms;

Z is $-CH_2CH_2-$; $-CH=CH$;

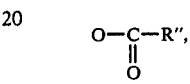

Y is thietanyl or alkyl-substituted thietanyl containing up to a total of 8 carbon atoms;

B' is H or an amino protecting group with the proviso that when Z is

B' is not H;
and food acceptable salts thereof.

2. The compound according to claim 1 wherein Z is a tetramethylthietanyl.

3. The compound according to claim 1 wherein Z is a trimethylthietanyl.

4. The compound according to claim 1 wherein Z is a dimethylthietanyl.

5. The compound according to claim 1 wherein Z is 2,2,4,4-tetramethylthietan-3-yl.

6. The compound according to claim 1 wherein Z is 2,4-dimethylthietan-3-yl.

7. The compound according to claim 1 wherein Z is 2,2-dimethylthietan-3-yl.

8. The compound according to claim 1 wherein the amino protecting group is $COCF_3$, $COCCl_3$, and $CO-NAr-X$, wherein Ar is aryl, X is $NO_2$, CN, COOR'', COR'', $SO_2R''$, halo, carboxy, $SO_3H$, $SO_3R''$, $SO_2NR''R''$, $SO_2NH$ R'', $SO_2NH_2$, $CONR''R''$, CONHR'', $CONH_2$, SOR'', $$O-C-R'',\ \overset{\|}{O}$$

OR'', $OSO_2R''$, $OCF_3$, $CH_2OR''$, $CH(OR'')_2$, $COCF_3$, $CF_3$, $CH_2CF_3$, $CCl_3$, $C_tF_{2t+1}$, and the like;
wherein
each R'' is the same or different and is $C_1-C_{12}$ alkyl and
t is an integer from 1–6.

9. The compound according to claim 1 which is N-α-L-aspartyl-2-amino-4-(2,2,4,4-tetramethylthietan-3-yl)trans-3-butene.

10. The compound according to claim 1 which is N-α-L-aspartyl-2-amino-4-(2,2,4,4-tetramethylthietan-3-yl)butane.

11. The compound according to claim 1 which is (2,2,4,4-tetramethylthietanyl) N-α-L-aspartyl-2-aminoisobutyrate.

12. The compound according to claim 1 which is N-Boc-L-aspartic acid-β-t-butyl ester-α-DL-2-amino-4-(2,2,4,4-tetramethyl)thietanyl-3-butanone.

13. The compound according to claim 1 which is N-α-L-aspartyl-DL-2-amino-4-(2,2,4,4-tetramethylthietanyl)-3-butanol.

14. A compound of the formula:

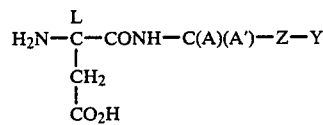

wherein
A is hydrogen, alkyl containing 1–3 carbon atoms, hydroxyalkyl containing 1–3 carbon atoms, alkoxymethyl wherein the alkoxy contains 1–3 carbon atoms or carbalkoxy wherein the alkoxy group contains 1–3 carbon atoms;

A' is hydrogen or alkyl containing 1–3 carbon atoms;

A and A' taken together with the carbon atom to which they are attached form cycloalkyl containing 3–4 carbon atoms;

Z is $-CH=CH-$; and

Y is thietanyl or alkyl-substituted thietanyl containing up to a total of 8 carbon atoms;
and food-acceptable salts thereof.

15. The compound according to claim 14 wherein Z is a tetramethylthietanyl.

16. The compound according to claim 14 wherein Z is a trimethylthietanyl.

17. The compound according to claim 14 wherein Z is a dimethylthietanyl.

18. The compound according to claim 14 wherein Z is 2,2,4,4-tetramethylthietan-3-yl.

19. The compound according to claim 14 wherein Z is 2,4-dimethylthietan-3-yl.

20. The compound according to claim 14 wherein Z is 2,2-dimethylthietan-3-yl.

21. A compound of the formula:

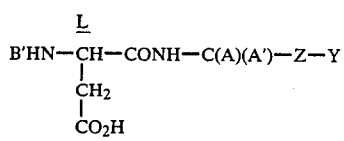

wherein
A is hydrogen, alkyl containing 1-3 carbon atoms, hydroxyalkyl containing 1-3 carbon atoms, alkoxymethyl wherein the alkoxy contains 1-3 carbon atoms or carbalkoxy wherein the alkoxy group contains 1-3 carbon atoms;
A' is hydrogen or alkyl containing 1-3 carbon atoms;
A and A' taken together with the carbon atom to which they are attached form cycloalkyl containing 3-4 carbon atoms;
Z is

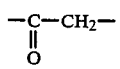

Y is thietanyl or alkyl-substituted thietanyl containing up to a total of 8 carbon atoms;
B' is an amine protecting group;
and food acceptable salts thereof.

22. The compound according to claim 21 wherein Z is a tetramethylthietanyl.

23. The compound according to claim 21 wherein Z is a trimethylthietanyl.

24. The compound according to claim 21 wherein Z is a dimethylthietanyl.

25. The compound according to claim 21 wherein Z is 2,2,4,4-tetramethylthietan-3-yl.

26. The compound according to claim 21 wherein Z is 2,4-dimethylthietan-3-yl.

27. The compound according to claim 21 wherein Z is 2,2-dimethylthietan-3-yl.

28. The compound according to claim 21 wherein B' is COCF$_3$, COCCl$_3$, and CONAr-X, wherein Ar is aryl, X is NO$_2$, CN, COOR", COR", SO$_2$R", halo, carboxy, SO$_3$H, SO$_3$R", SO$_2$NR"R", SO$_2$NH R", SO$_2$NH$_2$, CONR"R", CONHR", CONH$_2$, SOR",

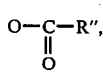

OR", OSO$_2$R", OCF$_3$, CH$_2$OR", CH(OR")$_2$, COCF$_3$, CF$_3$ CH$_2$CF$_3$, CCl$_3$, C$_t$F$_{2t+1}$, and the like;
wherein
each R" is the same or different and is C$_1$-C$_{12}$ alkyl and
t is an integer from 1-6.

29. A compound of the formula:

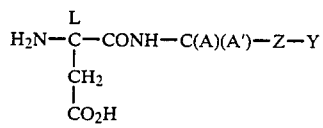

wherein
A is hydrogen, alkyl containing 1-3 carbon atoms, hydroxyalkyl containing 1-3 carbon atoms, alkoxymethyl wherein the alkoxy contains 1-3 carbon atoms or carbalkoxy wherein the alkoxy group contains 1-3 carbon atoms;
A' is hydrogen or alkyl containing 1-3 carbon atoms;
A and A' taken together with the carbon atom to which they are attached form cycloalkyl containing 3-4 carbon atoms;
Z is

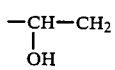

Y is thietanyl or alkyl-substituted thietanyl containing up to a total of 8 carbon atoms;
and food acceptable salts thereof.

30. The compound according to claim 29 wherein Z is a tetramethylthietanyl.

31. The compound according to claim 29 wherein Z is a trimethylthietanyl.

32. The compound according to claim 29 wherein Z is a dimethylthietanyl.

33. The compound according to claim 29 wherein Z is 2,2,4,4-tetramethylthietan-3-yl.

34. The compound according to claim 29 wherein Z is 2,4-dimethylthietan-3-yl.

35. The compound according to claim 29 wherein Z is 2,2-dimethylthietan-3-yl.

36. A compound of the formula:

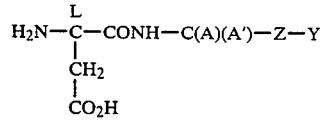

wherein
A is hydrogen, alkyl containing 1-3 carbon atoms, hydroxyalkyl containing 1-3 carbon atoms, alkoxymethyl wherein the alkoxy contains 1-3 carbon atoms or carbalkoxy wherein the alkoxy group contains 1-3 carbon atoms;
A' is hydrogen or alkyl containing 1-3 carbon atoms;
A and A' taken together with the carbon atom to which they are attached form cycloalkyl containing 3-4 carbon atoms;
Z is

Y is thietanyl or alkyl-substituted thietanyl containing up to a total of 8 carbon atoms;
and food acceptable salts thereof.

37. The compound according to claim 36 wherein Z is a tetramethylthietanyl.

38. The compound according to claim 36 wherein Z is a trimethylthietanyl.

39. The compound according to claim 36 wherein Z is a dimethylthietanyl.

40. The compound according to claim 36 wherein Z is 2,2,4,4-tetramethylthietan-3-yl.

41. The compound according to claim 36 wherein Z is 2,4-dimethylthietan-3-yl.

42. The compound according to claim 36 wherein Z is 2,2-dimethylthietan-3-yl.

43. An edible composition comprising a sweetening effective amount of a compound according to claim 1.

44. An edible composition according to claim 43 which further comprises a food acceptable carrier.

45. An edible composition according to claim 43 which is a beverage.

46. An edible composition according to claim 43 which is a gelatin dessert.

47. An edible composition according to claim 43 which is a milk-based composition.

48. An edible composition according to claim 43 which further comprises an additional sweetener.

49. An edible composition according to claim 48 wherein the additional sweetener is sucrose, fructose, corn syrup solids, dextrose, xylitol, sorbitol, mannitol, acetometa-aminobenzoic acid, meta-hydroxybenzoic acid, cyclamate, chlorosucrose, or dihydrochalcone, hydrogenated glucose syrup, aspartame or other dipeptides, glycyrrhizin or stevioside or mixtures thereof.

* * * * *